US007494665B1

(12) United States Patent  
Ding et al.

(10) Patent No.: US 7,494,665 B1
(45) Date of Patent: Feb. 24, 2009

(54) POLYMERS CONTAINING SILOXANE MONOMERS

(75) Inventors: Ni Ding, San Jose, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 843 days.

(21) Appl. No.: 10/909,795

(22) Filed: Jul. 30, 2004

(51) Int. Cl.
A61F 2/00 (2006.01)
(52) U.S. Cl. .................................... 424/423
(58) Field of Classification Search ................ 424/422, 424/423, 424, 425, 426, 427, 429, 432
See application file for complete search history.

(56) References Cited

U.S. PATENT DOCUMENTS

| | | | | |
|---|---|---|---|---|
| 2,072,303 | A | 3/1937 | Herrmann et al. | 128/335.5 |
| 2,386,454 | A | 10/1945 | Frosch et al. | 260/78 |
| 3,773,737 | A | 11/1973 | Goodman et al. | 260/78 |
| 3,849,514 | A | 11/1974 | Gray, Jr. et al. | 260/857 |
| 4,226,243 | A | 10/1980 | Shalaby et al. | 128/335.5 |
| 4,254,248 | A * | 3/1981 | Friends et al. | 526/279 |
| 4,260,725 | A * | 4/1981 | Keogh et al. | 526/279 |
| 4,327,203 | A * | 4/1982 | Deichert et al. | 526/279 |
| 4,329,383 | A | 5/1982 | Joh | 428/36 |
| 4,343,931 | A | 8/1982 | Barrows | 528/291 |
| 4,355,147 | A * | 10/1982 | Deichert et al. | 526/264 |
| 4,529,792 | A | 7/1985 | Barrows | 528/291 |
| 4,611,051 | A | 9/1986 | Hayes et al. | 528/295.3 |
| 4,656,242 | A | 4/1987 | Swan et al. | 528/295.3 |
| 4,733,665 | A | 3/1988 | Palmaz | 128/343 |
| 4,800,882 | A | 1/1989 | Gianturco | 128/343 |
| 4,882,168 | A | 11/1989 | Casey et al. | 424/468 |
| 4,886,062 | A | 12/1989 | Wiktor | 128/343 |
| 4,931,287 | A | 6/1990 | Bae et al. | 424/484 |
| 4,941,870 | A | 7/1990 | Okada et al. | 600/36 |
| 4,977,901 | A | 12/1990 | Ofstead | 128/772 |
| 5,019,096 | A | 5/1991 | Fox, Jr. et al. | 623/1 |
| 5,100,992 | A | 3/1992 | Cohn et al. | 424/501 |
| 5,112,457 | A | 5/1992 | Marchant | 204/165 |
| 5,133,742 | A | 7/1992 | Pinchuk | 623/1 |
| 5,163,952 | A | 11/1992 | Froix | 623/1 |
| 5,165,919 | A | 11/1992 | Sasaki et al. | 424/488 |
| 5,219,980 | A | 6/1993 | Swidler | 528/272 |
| 5,258,020 | A | 11/1993 | Froix | 623/1 |
| 5,272,012 | A | 12/1993 | Opolski | 428/423.1 |
| 5,292,516 | A | 3/1994 | Viegas et al. | 424/423 |
| 5,298,260 | A | 3/1994 | Viegas et al. | 424/486 |
| 5,300,295 | A | 4/1994 | Viegas et al. | 424/427 |
| 5,306,501 | A | 4/1994 | Viegas et al. | 424/423 |
| 5,306,786 | A | 4/1994 | Moens et al. | 525/437 |
| 5,328,471 | A | 7/1994 | Slepian | 604/101 |
| 5,330,768 | A | 7/1994 | Park et al. | 424/501 |
| 5,380,299 | A | 1/1995 | Fearnot et al. | 604/265 |
| 5,397,848 | A * | 3/1995 | Yang et al. | 525/477 |
| 5,408,999 | A * | 4/1995 | Singh et al. | 600/342 |
| 5,417,981 | A | 5/1995 | Endo et al. | 424/486 |
| 5,430,121 | A * | 7/1995 | Pudleiner et al. | 528/28 |
| 5,447,724 | A | 9/1995 | Helmus et al. | 424/426 |
| 5,455,040 | A | 10/1995 | Marchant | 424/426 |
| 5,462,990 | A | 10/1995 | Hubbell et al. | 525/54.1 |
| 5,464,650 | A | 11/1995 | Berg et al. | 427/2.3 |
| 5,485,496 | A | 1/1996 | Lee et al. | 378/64 |
| 5,516,881 | A | 5/1996 | Lee et al. | 528/320 |
| 5,569,463 | A | 10/1996 | Helmus et al. | 424/426 |
| 5,578,073 | A | 11/1996 | Haimovich et al. | 623/1 |
| 5,584,877 | A | 12/1996 | Miyake et al. | 623/1 |
| 5,605,696 | A | 2/1997 | Eury et al. | 424/423 |
| 5,607,467 | A | 3/1997 | Froix | 623/1 |
| 5,609,629 | A | 3/1997 | Fearnot et al. | 623/1 |
| 5,610,241 | A | 3/1997 | Lee et al. | 525/411 |
| 5,616,338 | A | 4/1997 | Fox, Jr. et al. | 424/423 |
| 5,624,411 | A | 4/1997 | Tuch | 604/265 |
| 5,628,730 | A | 5/1997 | Shapland et al. | 604/21 |
| 5,644,020 | A | 7/1997 | Timmermann et al. | 528/288 |
| 5,649,977 | A | 7/1997 | Campbell | 623/1 |
| 5,658,995 | A | 8/1997 | Kohn et al. | 525/432 |

(Continued)

FOREIGN PATENT DOCUMENTS

DE 42 24 401 1/1994

(Continued)

OTHER PUBLICATIONS

Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).

(Continued)

*Primary Examiner*—Sharon E. Kennedy
(74) *Attorney, Agent, or Firm*—Squire Sanders & Dempsey LLP

(57) ABSTRACT

A polymer of siloxanes as flexibility monomers and strength monomers is provided. It is also provided a polymer blend that contains a polymer formed of siloxane monomers and strength monomers and another biocompatible polymer. The biocompatible polymer or polymer blend described herein and optionally a bioactive agent can form a coating on an implantable device such as a drug-delivery stent. The implantable device can be used for treating or preventing a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

26 Claims, No Drawings

U.S. PATENT DOCUMENTS

| | | | | |
|---|---|---|---|---|
| 5,667,767 A | 9/1997 | Greff et al. | | 424/9.411 |
| 5,670,558 A | 9/1997 | Onishi et al. | | 523/112 |
| 5,674,242 A | 10/1997 | Phan et al. | | 606/198 |
| 5,679,400 A | 10/1997 | Tuch | | 427/2.14 |
| 5,700,286 A | 12/1997 | Tartaglia et al. | | 623/1 |
| 5,702,754 A | 12/1997 | Zhong | | 427/2.12 |
| 5,711,958 A | 1/1998 | Cohn et al. | | 424/423 |
| 5,716,981 A | 2/1998 | Hunter et al. | | 514/449 |
| 5,721,131 A | 2/1998 | Rudolph et al. | | 435/240 |
| 5,723,219 A | 3/1998 | Kolluri et al. | | 428/411.1 |
| 5,735,897 A | 4/1998 | Buirge | | 623/12 |
| 5,746,998 A | 5/1998 | Torchilin et al. | | 424/9.4 |
| 5,759,205 A | 6/1998 | Valentini | | 623/16 |
| 5,776,184 A | 7/1998 | Tuch | | 623/1 |
| 5,783,657 A | 7/1998 | Pavlin et al. | | 528/310 |
| 5,788,979 A | 8/1998 | Alt et al. | | 424/426 |
| 5,800,392 A | 9/1998 | Racchini | | 604/96 |
| 5,820,917 A | 10/1998 | Tuch | | 427/2.1 |
| 5,824,048 A | 10/1998 | Tuch | | 623/1 |
| 5,824,049 A | 10/1998 | Ragheb et al. | | 623/1 |
| 5,830,178 A | 11/1998 | Jones et al. | | 904/49 |
| 5,837,008 A | 11/1998 | Berg et al. | | 623/1 |
| 5,837,313 A | 11/1998 | Ding et al. | | 427/2.21 |
| 5,849,859 A | 12/1998 | Acemoglu | | 528/271 |
| 5,851,508 A | 12/1998 | Greff et al. | | 424/9.411 |
| 5,854,376 A | 12/1998 | Higashi | | 528/288 |
| 5,858,746 A | 1/1999 | Hubbell et al. | | 435/177 |
| 5,865,814 A | 2/1999 | Tuch | | 604/265 |
| 5,869,127 A | 2/1999 | Zhong | | 427/2.12 |
| 5,873,904 A | 2/1999 | Ragheb et al. | | 623/1 |
| 5,876,433 A | 3/1999 | Lunn | | 623/1 |
| 5,877,224 A | 3/1999 | Brocchini et al. | | 514/772.2 |
| 5,879,713 A | 3/1999 | Roth et al. | | 424/489 |
| 5,902,875 A | 5/1999 | Roby et al. | | 528/310 |
| 5,905,168 A | 5/1999 | Dos Santos et al. | | 562/590 |
| 5,910,564 A | 6/1999 | Gruning et al. | | 528/310 |
| 5,914,387 A | 6/1999 | Roby et al. | | 528/310 |
| 5,919,893 A | 7/1999 | Roby et al. | | 525/411 |
| 5,925,720 A | 7/1999 | Kataoka et al. | | 525/523 |
| 5,932,299 A | 8/1999 | Katoot | | 427/508 |
| 5,955,509 A | 9/1999 | Webber et al. | | 514/772.7 |
| 5,958,385 A | 9/1999 | Tondeur et al. | | 424/61 |
| 5,962,138 A | 10/1999 | Kolluri et al. | | 428/411.1 |
| 5,971,954 A | 10/1999 | Conway et al. | | 604/96 |
| 5,980,928 A | 11/1999 | Terry | | 424/427 |
| 5,980,972 A | 11/1999 | Ding | | 427/2.24 |
| 5,997,517 A | 12/1999 | Whitbourne | | 604/265 |
| 6,010,530 A | 1/2000 | Goicoechea | | 623/1 |
| 6,011,125 A | 1/2000 | Lohmeijer et al. | | 525/440 |
| 6,015,541 A | 1/2000 | Greff et al. | | 424/1.25 |
| 6,033,582 A | 3/2000 | Lee et al. | | 216/37 |
| 6,034,204 A | 3/2000 | Mohr et al. | | 528/328 |
| 6,042,875 A | 3/2000 | Ding et al. | | 427/2.24 |
| 6,051,576 A | 4/2000 | Ashton et al. | | 514/255 |
| 6,051,648 A | 4/2000 | Rhee et al. | | 525/54.1 |
| 6,054,553 A | 4/2000 | Groth et al. | | 528/335 |
| 6,056,993 A | 5/2000 | Leidner et al. | | 427/2.25 |
| 6,060,451 A | 5/2000 | DiMaio et al. | | 514/13 |
| 6,060,518 A | 5/2000 | Kabanov et al. | | 514/781 |
| 6,080,488 A | 6/2000 | Hostettler et al. | | 428/423.3 |
| 6,096,070 A | 8/2000 | Ragheb et al. | | 623/1 |
| 6,099,562 A | 8/2000 | Ding et al. | | 623/1.46 |
| 6,110,188 A | 8/2000 | Narciso, Jr. | | 606/153 |
| 6,110,483 A | 8/2000 | Whitbourne et al. | | 424/423 |
| 6,113,629 A | 9/2000 | Ken | | 623/1.1 |
| 6,120,491 A | 9/2000 | Kohn et al. | | 604/502 |
| 6,120,536 A | 9/2000 | Ding et al. | | 623/1.43 |
| 6,120,788 A | 9/2000 | Barrows | | 424/426 |
| 6,120,904 A | 9/2000 | Hostettler et al. | | 428/423.3 |
| 6,121,027 A | 9/2000 | Clapper et al. | | 435/180 |
| 6,129,761 A | 10/2000 | Hubbell | | 623/11 |
| 6,136,333 A | 10/2000 | Cohn et al. | | 424/423 |
| 6,143,354 A | 11/2000 | Koulik et al. | | 428/2.24 |
| 6,153,252 A | 11/2000 | Hossainy et al. | | 427/2.3 |
| 6,159,978 A | 12/2000 | Myers et al. | | 514/252.1 |
| 6,165,212 A | 12/2000 | Dereume et al. | | 623/1.13 |
| 6,172,167 B1 | 1/2001 | Stapert et al. | | 525/420 |
| 6,177,523 B1 | 1/2001 | Reich et al. | | 525/459 |
| 6,180,632 B1 | 1/2001 | Myers et al. | | 514/252.1 |
| 6,203,551 B1 | 3/2001 | Wu | | 606/108 |
| 6,211,249 B1 | 4/2001 | Cohn et al. | | 514/772.1 |
| 6,214,901 B1 | 4/2001 | Chudzik et al. | | 523/113 |
| 6,231,600 B1 | 5/2001 | Zhong | | 623/1.42 |
| 6,240,616 B1 | 6/2001 | Yan | | 29/527.2 |
| 6,245,753 B1 | 6/2001 | Byun et al. | | 514/56 |
| 6,245,760 B1 | 6/2001 | He et al. | | 514/234.8 |
| 6,248,129 B1 | 6/2001 | Froix | | 623/1.42 |
| 6,251,136 B1 | 6/2001 | Guruwaiya et al. | | 623/1.46 |
| 6,254,632 B1 | 7/2001 | Wu et al. | | 623/1.15 |
| 6,258,121 B1 | 7/2001 | Yang et al. | | 623/1.46 |
| 6,258,371 B1 | 7/2001 | Koulik et al. | | 424/422 |
| 6,262,034 B1 | 7/2001 | Mathiowitz et al. | | 514/44 |
| 6,270,788 B1 | 8/2001 | Koulik et al. | | 424/423 |
| 6,277,449 B1 | 8/2001 | Kolluri et al. | | 427/289 |
| 6,283,947 B1 | 9/2001 | Mirzaee | | 604/264 |
| 6,283,949 B1 | 9/2001 | Roorda | | 604/288.02 |
| 6,284,305 B1 | 9/2001 | Ding et al. | | 427/2.28 |
| 6,287,628 B1 | 9/2001 | Hossainy et al. | | 427/2.3 |
| 6,299,604 B1 | 10/2001 | Ragheb et al. | | 604/265 |
| 6,306,176 B1 | 10/2001 | Whitbourne | | 623/23.59 |
| 6,331,313 B1 | 12/2001 | Wong et al. | | 424/427 |
| 6,335,029 B1 | 1/2002 | Kamath et al. | | 424/423 |
| 6,344,035 B1 | 2/2002 | Chudzik et al. | | 604/265 |
| 6,346,110 B2 | 2/2002 | Wu | | 606/108 |
| 6,358,556 B1 | 3/2002 | Ding et al. | | 427/2.24 |
| 6,379,381 B1 | 4/2002 | Hossainy et al. | | 623/1.42 |
| 6,387,379 B1 | 5/2002 | Goldberg et al. | | 424/400 |
| 6,395,326 B1 | 5/2002 | Castro et al. | | 427/2.24 |
| 6,419,692 B1 | 7/2002 | Yang et al. | | 623/1.15 |
| 6,451,373 B1 | 9/2002 | Hossainy et al. | | 427/2.25 |
| 6,482,834 B2 | 11/2002 | Spada et al. | | 514/311 |
| 6,494,862 B1 | 12/2002 | Ray et al. | | 604/96.01 |
| 6,503,538 B1 | 1/2003 | Chu et al. | | 424/497 |
| 6,503,556 B2 | 1/2003 | Harish et al. | | 427/2.24 |
| 6,503,954 B1 | 1/2003 | Bhat et al. | | 514/772.2 |
| 6,506,437 B1 | 1/2003 | Harish et al. | | 427/2.25 |
| 6,524,347 B1 | 2/2003 | Myers et al. | | 514/252.1 |
| 6,527,801 B1 | 3/2003 | Dutta | | 623/1.46 |
| 6,527,863 B1 | 3/2003 | Pacetti et al. | | 118/500 |
| 6,528,526 B1 | 3/2003 | Myers et al. | | 214/311 |
| 6,530,950 B1 | 3/2003 | Alvarado et al. | | 623/1.13 |
| 6,530,951 B1 | 3/2003 | Bates et al. | | 623/1.45 |
| 6,540,776 B2 | 4/2003 | Sanders Millare et al. | | 623/1.15 |
| 6,544,223 B1 | 4/2003 | Kokish | | 604/103.01 |
| 6,544,543 B1 | 4/2003 | Mandrusov et al. | | 424/422 |
| 6,544,582 B1 | 4/2003 | Yoe | | 427/2.24 |
| 6,555,157 B1 | 4/2003 | Hossainy | | 427/2.24 |
| 6,558,733 B1 | 5/2003 | Hossainy et al. | | 427/2.24 |
| 6,565,659 B1 | 5/2003 | Pacetti et al. | | 118/500 |
| 6,572,644 B1 | 6/2003 | Moein | | 623/1.11 |
| 6,585,755 B2 | 7/2003 | Jackson et al. | | 623/1.15 |
| 6,585,765 B1 | 7/2003 | Hossainy et al. | | 623/1.45 |
| 6,585,926 B1 | 7/2003 | Mirzaee | | 264/400 |
| 6,605,154 B1 | 8/2003 | Villareal | | 118/500 |
| 6,616,765 B1 | 9/2003 | Castro et al. | | 623/1.45 |
| 6,623,448 B2 | 9/2003 | Slater | | 604/95.01 |
| 6,625,486 B2 | 9/2003 | Lundkvist et al. | | 604/21 |
| 6,645,135 B1 | 11/2003 | Bhat | | 600/3 |
| 6,645,195 B1 | 11/2003 | Bhat et al. | | 604/528 |
| 6,656,216 B1 | 12/2003 | Hossainy et al. | | 623/1.13 |
| 6,656,506 B1 | 12/2003 | Wu et al. | | 424/489 |
| 6,660,034 B1 | 12/2003 | Mandrusov et al. | | 623/1.42 |
| 6,663,662 B2 | 12/2003 | Pacetti et al. | | 623/1.13 |
| 6,663,880 B1 | 12/2003 | Roorda et al. | | 424/423 |

| Patent Number | Date | Inventor | Class |
|---|---|---|---|
| 6,666,880 B1 | 12/2003 | Chiu et al. | 623/1.11 |
| 6,673,154 B1 | 1/2004 | Pacetti et al. | 118/500 |
| 6,673,385 B1 | 1/2004 | Ding et al. | 427/2.28 |
| 6,689,099 B2 | 2/2004 | Mirzaee | 604/107 |
| 6,695,920 B1 | 2/2004 | Pacetti et al. | 118/500 |
| 6,706,013 B1 | 3/2004 | Bhat et al. | 604/96.01 |
| 6,709,514 B1 | 3/2004 | Hossainy | 118/52 |
| 6,712,845 B2 | 3/2004 | Hossainy | 623/1.42 |
| 6,713,119 B2 | 3/2004 | Hossainy et al. | 427/2.25 |
| 6,716,444 B1 | 4/2004 | Castro et al. | 424/422 |
| 6,723,120 B2 | 4/2004 | Yan | 623/1.15 |
| 6,733,768 B2 | 5/2004 | Hossainy et al. | 424/426 |
| 6,740,040 B1 | 5/2004 | Mandrusov et al. | 600/439 |
| 6,743,462 B1 | 6/2004 | Pacetti | 427/2.24 |
| 6,749,626 B1 | 6/2004 | Bhat et al. | 623/1.1 |
| 6,753,071 B1 | 6/2004 | Pacetti et al. | 428/212 |
| 6,758,859 B1 | 7/2004 | Dang et al. | 623/1.15 |
| 6,759,054 B2 | 7/2004 | Chen et al. | 424/423 |
| 6,764,505 B1 | 7/2004 | Hossainy et al. | 623/1.15 |
| 6,858,218 B2 * | 2/2005 | Lai et al. | 424/422 |
| 2001/0007083 A1 | 7/2001 | Roorda | 623/1.15 |
| 2001/0014717 A1 | 8/2001 | Hossainy et al. | 525/60 |
| 2001/0018469 A1 | 8/2001 | Chen et al. | 523/121 |
| 2001/0020011 A1 | 9/2001 | Mathiowitz et al. | 514/44 |
| 2001/0029351 A1 | 10/2001 | Falotico et al. | 604/103.02 |
| 2001/0037145 A1 | 11/2001 | Guruwaiya et al. | 623/1.15 |
| 2001/0051608 A1 | 12/2001 | Mathiowitz et al. | 514/44 |
| 2002/0005206 A1 | 1/2002 | Falotico et al. | 128/898 |
| 2002/0007213 A1 | 1/2002 | Falotico et al. | 623/1.21 |
| 2002/0007214 A1 | 1/2002 | Falotico | 623/1.21 |
| 2002/0007215 A1 | 1/2002 | Falotico et al. | 623/1.21 |
| 2002/0009604 A1 | 1/2002 | Zamora et al. | 428/450 |
| 2002/0016625 A1 | 2/2002 | Falotico et al. | 623/1.13 |
| 2002/0032414 A1 | 3/2002 | Ragheb et al. | 604/265 |
| 2002/0032434 A1 | 3/2002 | Chudzik et al. | 604/890.1 |
| 2002/0051730 A1 | 5/2002 | Bodnar et al. | 422/33 |
| 2002/0071822 A1 | 6/2002 | Uhrich | 424/78.37 |
| 2002/0077693 A1 | 6/2002 | Barclay et al. | 623/1.13 |
| 2002/0082679 A1 | 6/2002 | Sirhan et al. | 623/1.15 |
| 2002/0087123 A1 | 7/2002 | Hossainy et al. | 604/198 |
| 2002/0091433 A1 | 7/2002 | Ding et al. | 623/1.2 |
| 2002/0094440 A1 | 7/2002 | Llanos et al. | 428/421 |
| 2002/0111590 A1 | 8/2002 | Davila et al. | 604/265 |
| 2002/0120326 A1 | 8/2002 | Michal | 623/1.15 |
| 2002/0123801 A1 | 9/2002 | Pacetti et al. | 623/1.46 |
| 2002/0142039 A1 | 10/2002 | Claude | 424/486 |
| 2002/0155212 A1 | 10/2002 | Hossainy | 427/2.25 |
| 2002/0165608 A1 | 11/2002 | Llanos et al. | 623/1.45 |
| 2002/0176849 A1 | 11/2002 | Slepian | 424/93.7 |
| 2002/0183581 A1 | 12/2002 | Yoe et al. | 600/3 |
| 2002/0188037 A1 | 12/2002 | Chudzik et al. | 523/112 |
| 2002/0188277 A1 | 12/2002 | Roorda et al. | 604/523 |
| 2003/0004141 A1 | 1/2003 | Brown | 514/152 |
| 2003/0028243 A1 | 2/2003 | Bates et al. | 623/1.15 |
| 2003/0028244 A1 | 2/2003 | Bates et al. | 623/1.15 |
| 2003/0031780 A1 | 2/2003 | Chudzik et al. | 427/2.1 |
| 2003/0032767 A1 | 2/2003 | Tada et al. | 528/310 |
| 2003/0036794 A1 | 2/2003 | Ragheb et al. | 623/1.15 |
| 2003/0039689 A1 | 2/2003 | Chen et al. | 424/468 |
| 2003/0040712 A1 | 2/2003 | Ray et al. | 604/173 |
| 2003/0040790 A1 | 2/2003 | Furst | 623/1.11 |
| 2003/0059520 A1 | 3/2003 | Chen et al. | 427/2.1 |
| 2003/0060877 A1 | 3/2003 | Falotico et al. | 623/1.42 |
| 2003/0065377 A1 | 4/2003 | Davila et al. | 623/1.13 |
| 2003/0072868 A1 | 4/2003 | Harish et al. | 427/2.24 |
| 2003/0073961 A1 | 4/2003 | Happ | 604/274 |
| 2003/0083646 A1 | 5/2003 | Sirhan et al. | 604/891.1 |
| 2003/0083739 A1 | 5/2003 | Cafferata | 623/1.42 |
| 2003/0097088 A1 | 5/2003 | Pacetti | 604/19 |
| 2003/0097173 A1 | 5/2003 | Dutta | 623/1.38 |
| 2003/0099712 A1 | 5/2003 | Jayaraman | 424/486 |
| 2003/0105518 A1 | 6/2003 | Dutta | 623/1.38 |
| 2003/0113439 A1 | 6/2003 | Pacetti et al. | 427/2.24 |
| 2003/0150380 A1 | 8/2003 | Yoe | 118/423 |
| 2003/0157241 A1 | 8/2003 | Hossainy et al. | 427/2.24 |
| 2003/0158517 A1 | 8/2003 | Kokish | 604/103.01 |
| 2003/0190406 A1 | 10/2003 | Hossainy et al. | 427/2.25 |
| 2003/0207020 A1 | 11/2003 | Villareal | 427/2.24 |
| 2003/0211230 A1 | 11/2003 | Pacetti et al. | 427/2.24 |
| 2004/0018296 A1 | 1/2004 | Castro et al. | 427/2.25 |
| 2004/0029952 A1 | 2/2004 | Chen et al. | 514/449 |
| 2004/0047978 A1 | 3/2004 | Hossainy et al. | 427/2.1 |
| 2004/0047980 A1 | 3/2004 | Pacetti et al. | 427/2.25 |
| 2004/0052858 A1 | 3/2004 | Wu et al. | 424/490 |
| 2004/0052859 A1 | 3/2004 | Wu et al. | 424/490 |
| 2004/0054104 A1 | 3/2004 | Pacetti | 526/242 |
| 2004/0060508 A1 | 4/2004 | Pacetti et al. | 118/264 |
| 2004/0062853 A1 | 4/2004 | Pacetti et al. | 427/2.1 |
| 2004/0063805 A1 | 4/2004 | Pacetti et al. | 523/113 |
| 2004/0071861 A1 | 4/2004 | Mandrusov et al. | 427/2.24 |
| 2004/0072922 A1 | 4/2004 | Hossainy et al. | 523/113 |
| 2004/0073298 A1 | 4/2004 | Hossainy | 623/1.46 |
| 2004/0086542 A1 | 5/2004 | Hossainy et al. | 424/423 |
| 2004/0086550 A1 | 5/2004 | Roorda et al. | 424/448 |
| 2004/0096504 A1 | 5/2004 | Michal | 424/471 |
| 2004/0098118 A1 | 5/2004 | Hossainy et al. | 623/1.42 |
| 2004/0247674 A1 * | 12/2004 | Haapakumpu et al. | 424/471 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |

| | | |
|---|---|---|
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |

OTHER PUBLICATIONS

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catherization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micellas as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatiable coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol)Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivodelivery to a solid tumor*, Journal of Controlled Release 50:79-92 (1998).

Hamurcu et al., *Preparation and Characterization of Block and Graft Copolymers Using Macroazoinitiators Having Siloxane Units*, Journal of Applied Polymer Science, vol. 62, 1415-1426 (1996).

Qin et al., *Polymerization of Methyl Methacrylate With a Thermal Iniferter: Diethyl 2,3-Dicyano-2,3-di(p-tolyl)succinate*, Journal of Applied Polymer Science, vol. 80, 2566-2572 (2001).

* cited by examiner

POLYMERS CONTAINING SILOXANE MONOMERS

BACKGROUND OF THE INVENTION

1. Field of the Invention

This invention generally relates to a polymeric material useful for medical application such as for coating an implantable device, one example of which is a stent.

2. Description of the Background

Although stents work well mechanically, the chronic issues of restenosis and, to a lesser extent, stent thrombosis remain. Pharmacological therapy in the form of a drug-delivery stent appears a feasible means to tackle these biologically derived issues. Polymeric coatings placed onto the stent serve to act both as the drug reservoir, and to control the release of the drug. One of the commercially available polymer coated products is stents manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition which includes a bioactive agent, a collagenous material, or a collagenous coating optionally containing or coated with other bioactive agents.

The nature of the coating polymers plays an important role in defining the surface properties of a coating. For example, an amorphous coating material having a very low glass transition temperature ($T_g$) induces unacceptable rheological behavior upon mechanical perturbation such as crimping, balloon expansion, etc. On the other hand, a high $T_g$, or highly crystalline coating material introduces brittle fracture in the high strain areas of the stent pattern.

Some of the currently used polymeric materials have some undesirable properties such as lack of sufficient elongation to use on a stent or low permeability to drugs. One such polymer is such as poly(vinylidene fluoride) (PVDF). Therefore, there is a need for new polymeric materials suitable for use as coating materials on implantable devices.

The present invention addresses such problems by providing a polymeric material for coating implantable devices.

SUMMARY OF THE INVENTION

Provided herein is a polymer containing siloxane monomers and monomers that provide strength to the polymer. The siloxane monomers can provide flexibility for the polymer. The strength monomers impart strength to the polymer. The polymer can be a random polymer. Alternatively, the polymer can be a block copolymer having a general formula of AB, ABA, or BAB, or a graft copolymer such as A-g-B or B-g-A, A being the polysiloxane block and B being the block formed of the strength monomers. The polymer is useful for coating an implantable device such as a stent.

In one embodiment, the polymer can be a random or block polymer having a general formula as shown below (Formula I):

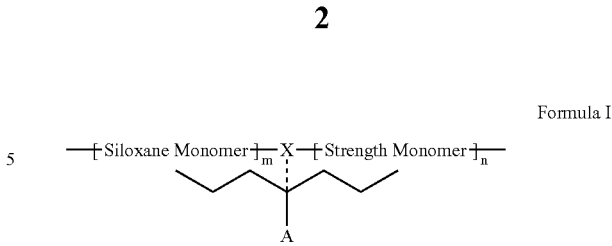

Formula I where m and n can be positive integers from, e.g., 1 to 100,000, 1 to 50,000, 1 to 10,000, 1 to 5,000, 1 to 1,000, 1 to 500, 1 to 100, or 1 to 50, where X can be absence, a linking group, a biobeneficial moiety or optionally a bioactive agent, and where A is an absence, a biobeneficial moiety or optionally a bioactive agent.

The bioactive agent A can physically or chemically attached to the polymer. The bioactive agent A can be stable or capable of being cleaved off under physiological conditions.

The siloxane monomers can be any siloxanes capable of polymerization. Such siloxanes can be, for example, dimethyl siloxane, methyl-phenol siloxane, or a fluorosiloxane such as methyl 3,3,3-trifluoropropyl siloxane. A general formula of such siloxanes is

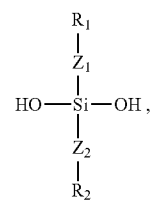

where $R_1$ and $R_2$ are independently H, halo groups such as F, Cl, Br and I, C1-C10 alkyl, C3-C10 cycloalkyl, substituted C1-C10 alkyl, haloalkyl such as fluoroalkyl, chloroalkyl, bromoalkyl, iodoalkyl, phenyl, substituted phenyl such as alkoxyphenyl, halophenyl and alkylphenyl, aryl, or substituted aryl such as alkoxyaryl, haloaryl and alkylaryl, and $Z_1$ and $Z_2$ are independently absence or oxygen (O).

The strength monomers can be any biocompatible monomers capable of imparting strength to the polymer. Some representative monomers include fluorinated monomers such as ethylene, propylene, vinylidene fluoride, hexafluoropropene, tetrafluoroethylene, chlorotrifluoroethylene, vinyl fluoride, and hydropentafluoropropene, high $T_g$ methacrylates such as methyl methacrylate, ethyl methacrylate, n-propyl methacrylate, and t-butyl methacrylate, styrene, methyl styrene, hydroxyl ethyl acrylate, 4-methoxyphenyl acrylate, t-butyl acrylate, o-tolyl acrylate, hydroxyl ethyl methacrylate, isotactic cyclohexyl methacrylate, cyclohexyl methacrylate, cyclohexyl acrylate, isopropyl methacrylate, 3,3-dimethylbutyl methacrylate, ethyl fluoromethacrylate and combinations thereof.

Some representative polymers of Formula I include, but are not limited to, polymers as shown in Formulae II-VI:

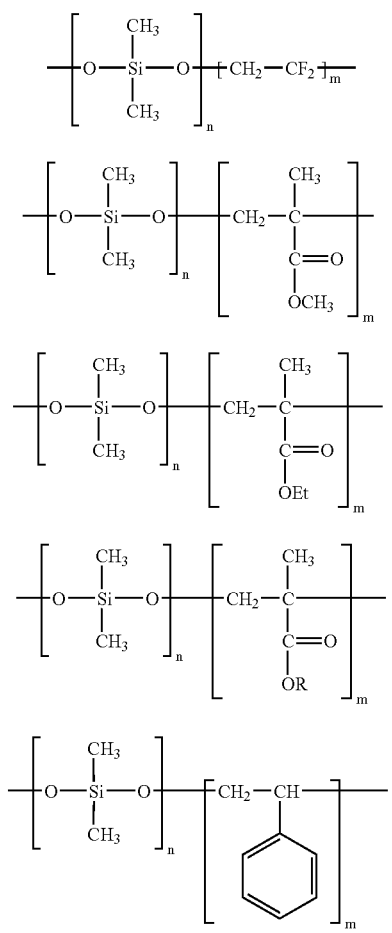

Formula II

Formula III

Formula IV

Formula V

Formula VI

In some embodiments, it is provided a polymer blend that includes a polymer that has siloxane monomers and at least one other biocompatible polymer. In one embodiment, the polymer that has siloxane monomers has a structure of formula I as defined above. In another embodiment, the blend can be made of a homopolymer of siloxane monomers defined above and homo or copolymer of strength monomers defined above.

The polymer or polymer blends described herein can be used to form a coating(s) on an implantable device. The implantable device can optionally include a bioactive agent or a biobeneficial compound that is blended therein. Some exemplary bioactive agents are paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-0-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, prodrugs thereof, co-drugs thereof, and combinations thereof. The implantable device can be implanted in a patient to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof

DETAILED DESCRIPTION

Polymers Containing Siloxane Monomers

Provided herein is a polymer containing siloxane monomers and monomers that provide strength to the polymer. The siloxane monomers can provide flexibility for the polymer. The strength monomers impart strength to the polymer. The polymer can be a random polymer. Alternatively, the polymer can be a block copolymer having a general formula of AB, ABA, or BAB, or a graft copolymer such as A-g-B or B-g-A, A being the polysiloxane block and B being the block formed of the strength monomers.

The polymer is useful for coating an implantable device such as a stent. A medical device, such as a stent, can also be made from this polymer.

In one embodiment, the polymer can be a random or block polymer having a general formula as shown below (Formula I):

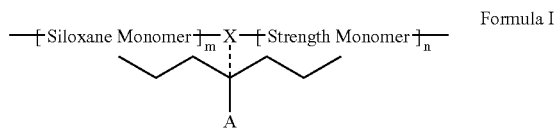

Formula I where m and n can be positive integers from, e.g., 1 to 100,000, 1 to 50,000, 1 to 10,000, 1 to 5,000, 1 to 1,000, 1 to 500, 1 to 100, or 1 to 50, where X can be absence, a linking group, a biobeneficial moiety or optionally a bioactive agent, and where A is an absence, a biobeneficial moiety or optionally a bioactive agent.

The bioactive agent A can physically or chemically attached to the polymer. The bioactive agent A can be stable or capable of being cleaved off under physiological conditions.

Linking groups X can be any linking agent commonly used in the art. Some of the representative linking agents linking agents include, for example, agents bearing hydroxyl, epoxide, carboxyl, amino, imide, aziridine, thiol, phosphoryl, aldehyde, anhydride, acyl halide, silyl, isocyanate, diisocyanate, carbodiimide, a dihydrazide, a multiaziridine, a multifunctional carbodiimide, isothiocynate or a diaamine functionalities, a polymer bearing a primary amine side group or side groups, N-hydroxy-succinamide, acryloxy terminated polyethylene glycol, and methacryloxy terminated polyethylene glycol. Other linking agents are listed in commercial catalogues such as Shearwater catalogue (Shearwater Polymers, Inc., Huntsville, Ala.) and Piercenet (http://www.piercenet.com/Objects/
View.cfm?type=File&ID=6ED00DF7-DE88-41C4-936A-
2ED95613340A) (Pierce Biotechnology, Inc., Rockford, Ill.).

The siloxane monomers can be any siloxanes capable of polymerization. Such siloxanes can be, for example, dimethyl siloxane, methyl-phenol siloxane, or a fluorosiloxane such as methyl 3,3,3-trifluoropropyl siloxane. A general formula of such siloxanes is

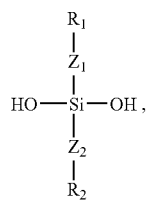

where $R_1$ and $R_2$ are independently H, halo groups such as F, Cl, Br and I, C1-C10 alkyl, C3-C10 cycloalkyl, substituted C1-C10 alkyl, haloalkyl such as fluoroalkyl, chloroalkyl, bromoalkyl, iodoalkyl, phenyl, substituted phenyl such as alkoxyphenyl, halophenyl and alkylphenyl, aryl, or substituted aryl such as alkoxyaryl, haloaryl and alkylaryl, and $Z_1$ and $Z_2$ are independently absence or oxygen (O).

The strength monomers can be any biocompatible monomers capable of imparting strength to the polymer. Some representative monomers include fluorinated monomers such as ethylene, propylene, vinylidene fluoride, hexafluoropropene, tetrafluoroethylene, chlorotrifluoroethylene, vinyl fluoride, and hydropentafluoropropene, high $T_g$ (e.g., $T_g$ above ambient temperature) methacrylates such as methyl methacrylate, ethyl methacrylate, n-propyl methacrylate, and t-butyl methacrylate, styrene, methyl styrene, hydroxyl ethyl acrylate, 4-methoxyphenyl acrylate, t-butyl acrylate, o-tolyl acrylate, hydroxyl ethyl methacrylate, isotactic cyclohexyl methacrylate, cyclohexyl methacrylate, cyclohexyl acrylate, isopropyl methacrylate, 3,3-dimethylbutyl methacrylate, ethyl fluoromethacrylate and combinations thereof.

Some representative polymers of Formula I include, but are not limited to, polymers as shown in Formulae II-VI:

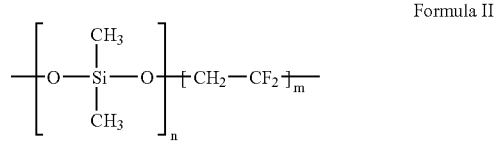

Formula II

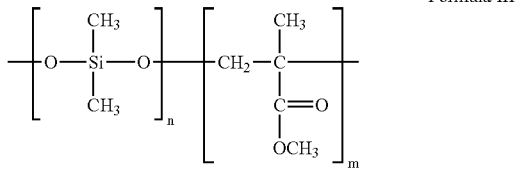

Formula III

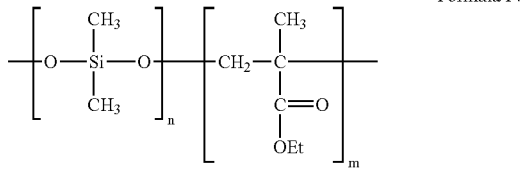

Formula IV

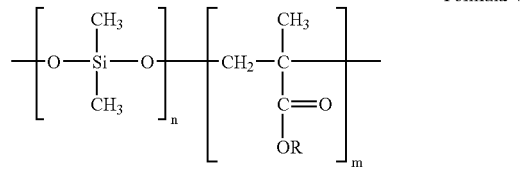

Formula V

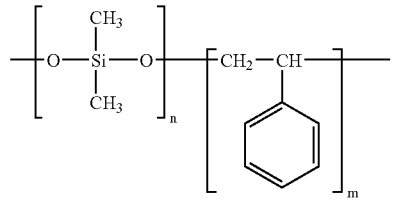

Formula VI

In some embodiments, it is provided a polymer blend that includes a polymer that has siloxane monomers and at least one other biocompatible polymer. In one embodiment, the polymer that has siloxane monomers has a structure of formula I as defined above. In another embodiment, the blend can be made of a homopolymer of siloxane monomers defined above and homo or copolymer of strength monomers defined above.

The polymer described herein can be synthesized by methods known in the art (see, for example, D. Braun, et al., Polymer Synthesis: Theory and Practice. Fundamentals, Methods, Experiments. 3rd Ed., Springer, 2001; Hans R. Kricheldorf, Handbook of Polymer Synthesis, Marcel Dekker Inc., 1992). For example, one method that can be used to make the polymer can be free radical methods (see, for example, D. Braun, et al., Polymer Synthesis: Theory and Practice. Fundamentals, Methods, Experiments. 3rd Ed., Springer, 2001; Hans R. Kricheldorf, Handbook of Polymer Synthesis, Marcel Dekker Inc., 1992). Polymerization in solvent can also be used to synthesize the polymer described herein.

Copolymerization prevents phase separation on a large scale. For systems where the reactivity ratios of the monomers greatly differ, a random polymerization will result in less and less of a random structure. Polymerizations that proceed step-wise via the formation of prepolymers may be used to achieve block structures (See, for example, J. Kopecek, et al., Prog. Polym. Sci, 9:34 (1983)).

For example, in one embodiment, the polymer described herein can be formed by quasi-random copolymerization by reacting a chlorinated monomer of the hard segment such as a dichlorofluoroalkane with hydroxylated silane such as dimethyl silanol. Alternatively, a dichlorosilane can react with a diol to form a polymer having siloxane monomers (Scheme 1).

Scheme 1

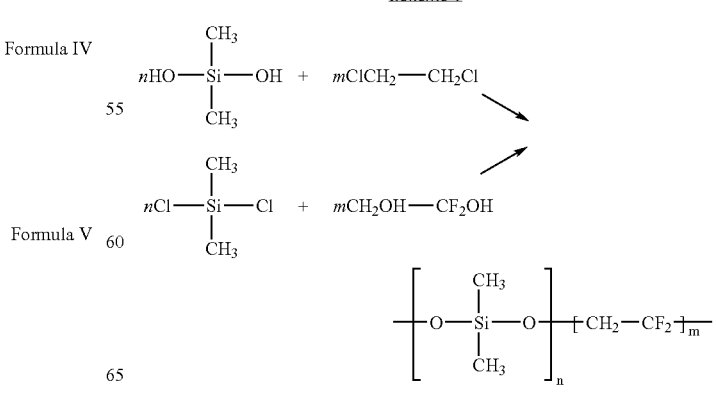

Polymers containing siloxane monomers with other strength monomers can be synthesized via reaction of a dialkylsilanol with a diol or via reaction of a dialkylsilanol with a diol in the presence of a tin catalyst. For example, poly(dimethyl siloxane-co-alkyl methacrylate) can be readily synthesized by these two routes (Scheme 2) and poly(dimethylsiloxane-co-styrene) can be synthesized by the reaction of dimethyldichlorosilane with phenyl ethylene glycol (Scheme 3).

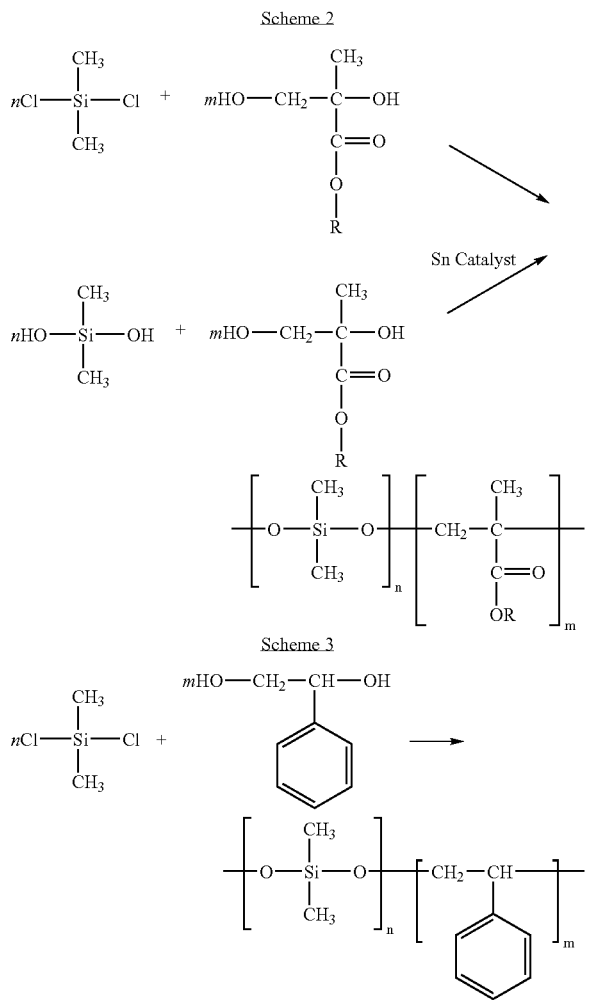

Block copolymers containing a siloxane block and one or more blocks of strength monomers can be prepared via atom-transfer radical polymerization (ATRP) (see, e.g., Honigfort, M. E.; et al., Polym. Prepr. 43:561 (2002)) or initiator-transfer agent-terminator (INIFERTER) polymerization (Qin, et al., J. Appl. Poly. Sci. 80(13):2566-72 (2001)). The ATRP or INIFERTER polymerization can produce a block of strength monomers with terminal functionality, which can be allowed to couple with one or two blocks of polysiloxane to generate a block copolymer containing one or more blocks of polysiloxane which imparts flexibility to the polymer and one or more blocks of strength monomers as hard segment(s) to impart mechanical strength to the polymer. In one embodiment, the polysiloxane block is polydimethylsiloxane. The hard segment can be, for example, a polystyrene block, a poly(methacrylate) block, or a poly(vinylidene fluoride) (PVDF) block. Both polystyrene and poly(methacrylate) are non-crystalline components with high $T_g$. PVDF has a low $T_g$ but is a crystalline polymer. By varying the ratio of a siloxane to monomers of the hard segment, one can generate thermoplastic polymer elastomer with tunable properties.

The block copolymer can also be prepared for example through free radical polymerization via macroazoinitiator (Hamurcu et al J. Appl. Polym Sci. 62: 1415-1426 (1996)). In this route, ax, co-amine terminated organofunctional polydimethylsiloxane (PDMS) can be condensed with, for example, 4,4'-azobis-4-cyanopentanoyl chloride (ACPC) to prepare macroazoinitiator containing siloxane units. Block copolymer or graft polymer containing PDMS and strength monomers were then derived by the polymerization of strength monomer initiated by macroazoinitiators.

Attaching a bioactive molecule to the molecule of formula I is well documented.

Polymer Blends

In another embodiment, the polymer of formulae I-VI can be blended with another biocompatible polymer to form a coating material for an implantable device or to form the implantable device itself. The biocompatible polymer can be biodegradable (bioerodable/bioabsorbable) or nondegradable. Representative examples of these biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalknaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, polyesters, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate) poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as and polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. PEO/PLA); polyalkylene oxides such as poly (ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly (methyl methacrylate)-PEG (PMMA-PEG), polydimethylsiloxane-co-PEG (PDMS-PEG), poly(vinylidene fluoride)-PEG (PVDF-PEG), PLURONICTM surfactants (polypropylene oxide-co-polyethylene glycol), poly(tetramethylene glycol), hydroxy functional poly(vinyl pyrrolidone), biomolecules such as collagen, chitosan, alginate, fibrin. fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, and combinations thereof. In some embodiments, the polymer can exclude any one of the aforementioned polymers.

As used herein, the terms poly(D,L-lactide) (PDLL), poly(L-lactide) (PLL), poly(D,L-lactide-co-glycolide) (PDLLG), and poly(L-lactide-co-glycolide) (PLLG) are used interchangeably with the terms poly(D,L-lactic acid) (PDLLA), poly(L-lactic acid) (PLLA), poly(D,L-lactic acid-co-glycolic acid) (PDLLAGA), and poly(L-lactic acid-co-glycolic acid) (PLLAGA), respectively.

Bioactive Agents

The polymers described herein can form a coating on an implantable device optionally with one or more bioactive agents. The agents can be blended, mixed, bonded, or conjugated to the polymers of the invention. Examples of such agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Other examples of drugs include antibodies, receptor ligands, and enzymes, adhesion peptides, oligosaccharides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Such agents can also include a prohealing drug that imparts a benign neointimal response characterized by controlled proliferation of smooth muscle cells and controlled deposition of extracellular matrix with complete luminal coverage by phenotypically functional (similar to uninjured, healthy intima) and morphologically normal (similar to uninjured, healthy intima) endothelial cells. Such agents can also fall under the genus of antineoplastic, cytostatic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycine from Pharmacia & Upjohn, Peapack N.J.), and mitomycin (e.g. Mutamycine from Bristol-Myers Squibb Co., Stamford, Conn.). Examples of such antiplatelets, anticoagulants, antifibrin, and antithrombins include heparinoids, hirudin, recombinant hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, antibody, and thrombin inhibitors such as Angiomax a (Biogen, Inc., Cambridge, Mass.). Examples of cytostatic agents include angiopeptin, angiotensin converting enzyme inhibitors such as captopril (e.g. Capoteno and Capozide® from Bristol-Myers Squibb Co., Stamford, Conn.), cilazapril or lisinopril (e.g. Prinivil® and Prinzide® from Merck & Co., Inc., Whitehouse Station, N.J.), actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Other drugs include calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium.

Other therapeutic substances or agents which may be appropriate include alpha-interferon, genetically engineered epithelial cells, antibodies such as CD-34 antibody, abciximab (REOPRO), and progenitor cell capturing antibody, prohealing drugs that promotes controlled proliferation of muscle cells with a normal and physiologically benign composition and synthesis products, enzymes, anti-inflammatory agents, antivirals, anticancer drugs, anticoagulant agents, free radical scavengers, steroidal anti-inflammatory agents, non-steroidal anti-inflammatory agents, antibiotics, nitric oxide donors, super oxide dismutases, super oxide dismutases mimics, 4-amino-2,2,6,6-tetramethylpiperidine- I -oxyl (4-amino-TEMPO), dexamethasone, clobetasol, aspirin, estradiol, tacrolimus, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, ABT-578, progenitor cell capturing antibody, pro-drugs thereof, co-drugs thereof, and a combination thereof. The foregoing substances are listed by way of example and are not meant to be limiting. Other active agents which are currently available or that may be developed in the future are equally applicable.

The dosage or concentration of the bioactive agent required to inhibit or promote a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. The bioactive compound can be incorporated into polymeric coating in a percent loading of between 0.01% and 70% by weight, more preferably between 5% and 50% by weight. Standard pharmacological test procedures to determine dosages are understood by one of ordinary skill in the art.

Biobeneficial Material

The polymer described herein can be used to coat an implantable device, one example of which is a stent, or forming an implantable device with a biobeneficial material. The biobeneficial can be blended, mixed, bonded, or conjugated to the polymers of the invention. The biobeneficial material can be a polymeric material or non-polymeric material. The biobeneficial material is preferably flexible when present as a discrete layer, or confers elastic properties in a blend or copolymer, and is biocompatible and/or biodegradable, more preferably non-toxic, non-antigenic and non-immunogenic.

A biobeneficial material is one which enhances the biocompatibility of a device by being non-fouling, hemocompatible, actively non-thrombogenic, or anti-inflammatory, all without depending on the release of a pharmaceutically active agent. As used herein, the term non-fouling is defined as preventing, delaying or reducing the amount of formation of protein build-up caused by the body's reaction to foreign material and can be used interchangeably with the term "antifouling."

Representative biobeneficial materials include, but are not limited to, polyethers such as poly(ethylene glycol), copoly(ether-esters) (e.g. PEO/PLA); polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropyl methacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilyl-propyl methacrylate (TMSPMA), polystyrene-polyisoprene-polystyrene-co-PEG (SIS-PEG), polystyrene-PEG, poly-isobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONICTM surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, and combinations thereof In some embodiments, the polymer can exclude any one of the aforementioned polymers.

In a preferred embodiment, the biobeneficial material is a block copolymer comprising flexible poly(ethylene glycol) terephthalate)/poly(butylenes terephthalate) (PEGT/PBT) segments (PolyActive™). These segments are biocompatible, non-toxic, non-antigenic and non-immunogenic. Previous studies have shown that the PolyActive™ top coat decreases the thrombosis and embolism formation on stents. PolyActive™ is generally expressed in the form of xPEG-TyPBTz, in which x is the molecular weight of PEG, y is percentage of PEGT, and z is the percentage of PBT. A specific PolyActive™ polymer can have various ratios of the PEG, ranging from about 1% to about 99%, e.g., about 10% to about 90%, about 20% to about 80%, about 30% to about 70%, about 40% to about 60% PEG. The PEG for forming PolyActive™ can have a molecular weight ranging from about 300 Daltons to about 100,000 Daltons, e.g., about 300 Daltons, about 500 Daltons, about 1,000 Daltons, about 5,000 Daltons, about 10,000 Daltons, about 20,000 Daltons, or about 50,000 Daltons.

In another preferred embodiment, the biobeneficial material can be a polyether such as polyehthylene glycol (PEG) or polyalkylene oxide.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35NN," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Use

In accordance with embodiments of the invention, a coating of the various described embodiments can be formed on an implantable device or prosthesis, e.g., a stent. In some embodiments, the body of the stent itself can be made from materials including the embodiments of the invention. For coatings including one or more active agents, the agent will retain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth prophetic examples. All parameters and data are not to be construed to unduly limit the scope of the embodiments of the invention.

Example 1

Polystyrene-b-polydimethylsiloxane (PS-b-PDMS) is purchased from Polymer Source Inc. Montreal Canada (www.polymersource.com) (Product Cat No.: P2617-SDMS, and PS/PDMS=36/14.8). 2% of PS-b-PDMS and 0.5% everolimus solution in chloroform-xylene (80:20) mixture can be prepared by adding 2 g of PS-b-PDMS and 0.5 g of everolimus into 78 gram of chloroform and 19.5 g of xylene mixture. The solution is shaken at room temperature until the drug and polymer fully dissolved. Alternatively, the suspension can be put in the oven at 50° C. for 1-2 hrs to speed up the polymer and drug dissolution.

The coating process can be briefly described as follows. A Vision 3×18 mm stent is pre-weighed, secured in the coating mandrel and mounted on a spray-coater. The polymer-drug solution is spray-coated on the stents with a flow rate of 20 µg per pass. The coating is dried in between from a dry air nozzle. After the coating weight is built about 500 µg, the coating is done. The stent is then dried in the oven at preset temperature, e.g. 50° C. The drug release rate can be measured in 2% porcine serum albumin.

Example 2

Polymethyl methacrylate-b-polydimethylsiloxane (PMMA-b-PDMS) is purchased from Polymer Source Inc. Montreal Canada (Product Cat. No.: P2493-DMSMMA, and PMMA/PDMS=20/8). 2% of PMMA-b-PDMS and 1% everolimus solution in chloroform-xylene (80:20) mixture is prepared by adding 2 g of PMMA-b-PDMS and 1 g of everolimus into 77.6 g of chloroform and 19.4 gram of xylene mixture. The solution is shaken at room temperature until the drug and polymer fully dissolved. Alternatively, the suspension can be put in the oven at 50° C. for 1-2 hrs to speed up the polymer and drug dissolution.

The solution can be coated onto a stent as described in Example 1.

Example 3

Poly(t-butyl acrylate-b-dimethylsiloxane) (PtBuA-b-PDMS) is purchased from Polymer Source Inc. Montreal Canada (Product Cat. No.: P2591-DMStBuA, and PtBuA/PDMS=18/8). 2% PtBuA-b-PDMS and 0.75% everolimus solution in chloroform-xylene (80:20) mixture is prepared by adding 2 g of PMMA-b-PDMS and 1 g of everolimus into 77.6 g of chloroform and 19.4 gram of xylene mixture. The solution is shaken at room temperature until the drug and polymer fully dissolved. Alternatively, the suspension can be put in the oven at 50° C. for 1-2 hrs to speed up the polymer and drug dissolution.

The solution can be coated onto a stent as described in Example 1.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A biocompatible polymer comprising siloxane monomers that impart flexibility to the polymer and monomers that impart mechanical strength to the polymer wherein the polymer has the structure of formula I:

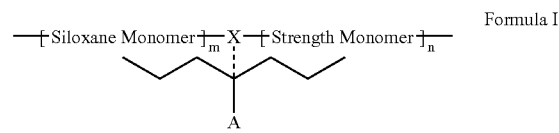

Formula I wherein m and n are independently positive integers,
wherein X is an absence, a linking group, a biobeneficial moiety or optionally a bioactive agent, and
wherein A is an absence, a biobeneficial moiety or optionally a bioactive agent,
wherein the siloxane monomer is derived from a compound having the formula of

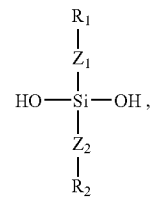

where $R_1$ and $R_2$ are independently H, F, Cl, Br, I, C1-C10 alkyl, C3-C10 cycloalkyl, substituted C1-C10 alkyl, haloalkyl, fluoroalkyl, chloroalkyl, bromoalkyl, iodoalkyl, phenyl, substituted phenyl, alkoxyphenyl, halophenyl and alkylphenyl, aryl, or substituted aryl, alkoxyaryl, haloaryl and alkylaryl, and $Z_1$ and $Z_2$ are independently absence or oxygen (O).

2. The biocompatible polymer of claim 1, wherein $R_1$ and $R_2$ are independently fluoroalkyl groups.

3. The biocompatible polymer of claim 1 wherein the strength monomer is selected from the group consisting of ethylene, propylene, vinylidene fluoride, hexafluoropropene, tetrafluoroethylene, chlorotrifluoroethylene, vinyl fluoride, and hydropentafluoropropene, high $T_g$ methacrylates, methyl methacrylate, ethyl methacrylate, n-propyl methacrylate, t-butyl methacrylate, styrene, methyl styrene, hydroxyl ethyl acrylate, 4-methoxyphenyl acrylate, t-butyl acrylate, o-tolyl acrylate, hydroxyl ethyl methacrylate, isotactic cyclohexyl methacrylate, cyclohexyl methacrylate, cyclohexyl acrylate, isopropyl methacrylate, 3,3-dimethylbutyl methacrylate, ethyl fluoromethacrylate and combinations thereof.

4. The biocompatible polymer of claim 1 having a structure of any of formulae II-VI:

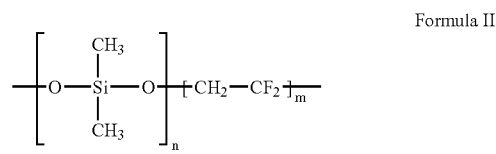

Formula II

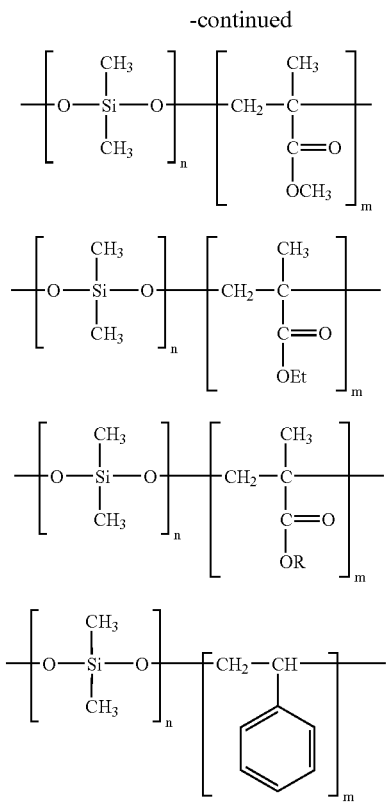

wherein m and n are positive integers.

5. A biocompatible polymer blend comprising the biocompatible polymer of claim 4 and at least one other biocompatible polymer.

6. A biocompatible polymer blend comprising the biocompatible polymer of claim 1 and at least one other biocompatible polymer.

7. A biocompatible polymer blend comprising the biocompatible polymer of claim 2 and at least one other biocompatible polymer.

8. An implantable device having a biocompatible coating thereon, wherein the biocompatible coating comprises the biocompatible polymer of claim 1.

9. An implantable device having a biocompatible coating thereon, wherein the biocompatible coating comprises the biocompatible polymer of claim 2.

10. An implantable device having a biocompatible coating thereon, wherein the biocompatible coating comprises the biocompatible polymer of claim 3.

11. An implantable device having a biocompatible coating thereon, wherein the biocompatible coating comprises the biocompatible polymer of claim 4.

12. An implantable device having a biocompatible coating thereon, wherein the biocompatible coating comprises the polymer blend of claim 5.

13. An implantable device having a biocompatible coating thereon, wherein the biocompatible coating comprises the polymer blend of claim 6.

14. An implantable device having a biocompatible coating thereon, wherein the biocompatible coating comprises the polymer blend of claim 7.

15. The implantable device of claim 8 which is a drug-delivery stent, wherein the coating further comprises a bioactive agent.

16. The implantable device of claim 9 which is a drug-delivery stent, wherein the coating further comprises a bioactive agent.

17. The implantable device of claim 10 which is a drug-delivery stent, wherein the coating further comprises a bioactive agent.

18. The implantable device of claim 11 which is a drug-delivery stent, wherein the coating further comprises a bioactive agent.

19. The implantable device of claim 12 which is a drug-delivery stent, wherein the coating further comprises a bioactive agent.

20. The implantable device of claim 13 which is a drug-delivery stent, wherein the coating further comprises a bioactive agent.

21. The implantable device of claim 14 which is a drug-delivery stent, wherein the coating further comprises a bioactive agent.

22. The drug-delivery stent of claim 15, wherein the bioactive agent is selected from the group consisting of paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, progenitor cell capturing antibody, prohealing drugs, prodrugs thereof, co-drugs thereof, and a combination thereof.

23. A method of treating a disorder in a patient comprising implanting in the patient the implantable device of claim 15, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

24. A biocompatible polymer blend comprising the biocompatible polymer of claim 3 and at least one other biocompatible polymer.

25. An implantable device having a biocompatible coating thereon, wherein the biocompatible coating comprises the polymer blend of claim 24.

26. The implantable device of claim 25 which is a drug-delivery stent, wherein the coating further comprises a bioactive agent.

* * * * *